United States Patent [19]

Rosenthal

[11] 4,017,192
[45] Apr. 12, 1977

[54] OPTICAL ANALYSIS OF BIOMEDICAL SPECIMENS

[75] Inventor: Robert D. Rosenthal, Gaithersburg, Md.

[73] Assignee: Neotec Corporation, Silver Spring, Md.

[22] Filed: Feb. 6, 1975

[21] Appl. No.: 547,658

[52] U.S. Cl. .................... 356/201; 356/39; 356/51
[51] Int. Cl.² ............................... G01N 21/22
[58] Field of Search ............ 356/39, 188, 51, 201

[56] References Cited

UNITED STATES PATENTS

| | | | |
|---|---|---|---|
| 2,708,515 | 5/1955 | Bliss | 356/53 |
| 3,327,117 | 6/1967 | Kamentsky | 356/36 |
| 3,327,119 | 6/1967 | Kamentsky | 356/51 |
| 3,540,824 | 11/1970 | Fonda et al. | 356/53 |
| 3,613,884 | 10/1971 | Van Gaalen | 356/53 |
| 3,740,144 | 6/1973 | Walker | 356/53 |
| 3,861,788 | 1/1975 | Webster | 356/188 |
| 3,877,818 | 4/1975 | Button et al. | 356/51 |

*Primary Examiner*—John K. Corbin
*Assistant Examiner*—Richard A. Rosenberger
*Attorney, Agent, or Firm*—Lane, Aitken, Dunner & Ziems

[57] ABSTRACT

A technique for automatic detection of abnormalities, particularly pathology, in biomedical specimens. Light transmittance or reflectance data over a large number of wavelengths for numerous samples are correlated mathematically with conventional clinical results to select test wavelengths and constants for a correlation equation. Optical instrumentation with an analog or digital computer applies the resulting correlation equation to the spectral data on a given specimen at the test wavelengths to determine quantitatively the presence of the abnormality.

13 Claims, 8 Drawing Figures

OPTICAL ANALYSIS OF BIOMEDICAL SPECIMENS

CROSS-REFERENCE TO RELATED APPLICATIONS

The subject matter of this application is related to that of U.S. Pat. No. 3,765,775 to Eugene R. Gannssle and Donald R. Webster, issued Oct. 16, 1973 entitled "Optical Quality Analyzer", U.S. Pat. No. 3,861,788 issued Jan. 21, 1975 to Donald R. Webster entitled "Optical Analyzer for Agricultural Products", and U.S. patent application, Ser. No. 283,270, filed Aug. 24, 1972 by Donald R. Webster, assigned to the assignee of this application. U.S. Pat. No. 3,861,788 in its entirety is incorporated herein by reference.

BACKGROUND OF THE INVENTION

The invention relates generally to the field of biomedical pathology and instruments for measuring and analyzing the optical properties of organic materials.

In the past, abnormalities in biomedical cellular material, for example malignant cells in a cervical biopsy, have had to be subjected to microscopic investigation by laboratory technicians specially trained in pathology. The use of qualitative visible and near-infrared spectrophotometry is, however, well established in the clinical laboratory for certain kinds of tests. Nevertheless, the use of spectral absorption techniques for quantitative analysis has had little, if any, clinical application.

U.S. Pat. No. 3,861,788 describes an optical analyzer designed to obtain reflectivity data from agricultural specimens such as grain and to determine the percent of various constitutents, particularly protein, water and oil by means of analog computation of the values of linear functions of the variables $\Delta OD$, the difference in optical density at several characteristic wavelength pairs.

Cancer of the uterus is the number one killer of women in the U.S.. Pap smears and cervical scrapings provide tissue specimens which are analyzed in the laboratory to diagnose uterine cancer. Only a small percentage of the nation's women have pap smears or scrapings taken regularly. If every woman in the U.S. had a pap smear taken and analyzed once a year, the death rate from uterine cancer would be drastically reduced because it is susceptible to early treatment. However, because pap smears and cervical scrapings require tedious microscopic analysis by trained laboratory technicians, there is no way that pap smears from every woman in the United States just once a year could ever be analyzed, given the limited availability of laboratory technicians and facilities. Hence, the interest in developing an instrument which will automatically, instantaneously diagnose cancerous biopsies is grounded in the realization that this is the only way that an effective nationwide program of uterine cancer detection can be carried out at all. No previous systems are adequate to this challenge.

SUMMARY OF THE INVENTION

In a technique for automatic detection of abnormalities, particularly pathology, in biomedical specimens, light transmittance or reflectance data over a large number of wavelengths for numerous samples are correlated, for example by multiple linear regression analysis, with conventional clinical results to select test wavelengths and constants for a correlation equation. Optical instrumentation with an analog or digital computer applies the resulting correlation equation to the spectral data on a given specimen at the test wavelengths determine quantitatively the presence of the abnormality. Specific examples are given for cervical cancer, cancer in mice and rats, and contaminated serum. In one form of instrumentation, an automatic monochromator, in the form of a rotatable paddle-wheel of filters, illuminates the specimen with progressively shifting narrow band radiation. The output of a photodetector, positioned to receive light transmitted through the specimen, is sampled to yield values indicative of transmissivity at the test wavelengths. In one embodiment, these values are converted to optical density and a plurality of stored optical density values at different wavelengths are manipulated by an analog computer programmed to perform a linear calculation. In another embodiment, the output of the photodetector is converted to digital form and fed to a digital computer adapted to store a plurality of values about each test wavelength and to perform a programmed sequence of operations to produce values at each test wavelength of the ratio of a derivative of transmissivity of the specimen to absolute transmissivity. The value of a linear function of these ratios indicates a specific abnormality.

DETAILED DESCRIPTION

Figure 1:
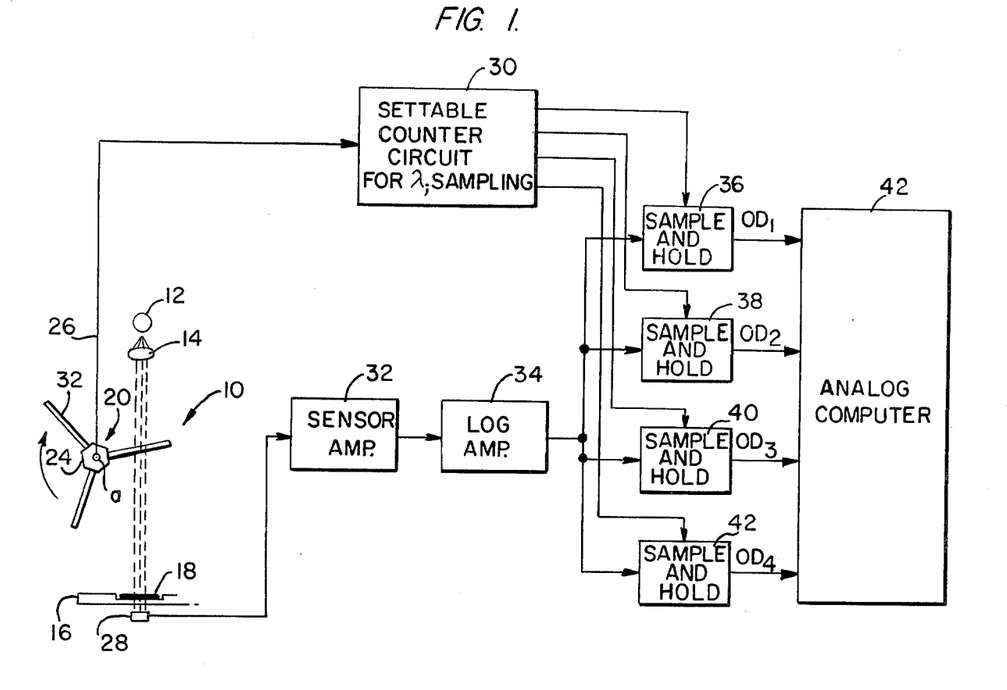
FIG. 1 is a block and schematic diagram illustrating apparatus for carrying out one of the techniques of the invention.
Figure 2:
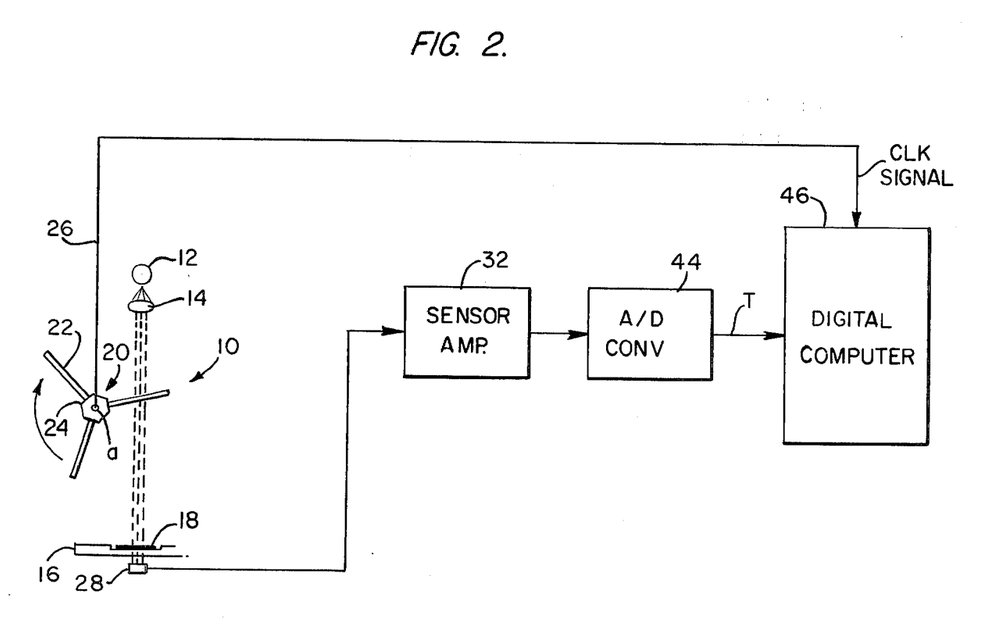
FIG. 2 is a block and schematic diagram for carrying out another of the techniques of the invention.

The optical instrumentation 10 in FIGS. 1 and 2 includes an infrared lamp 12 which directs wideband light through a lens 14 to illuminate a focused area on a sample drawer 16. The drawer 16 is adapted to carry a specimen 18 which may be in liquid, solid or gaseous form. The sample drawer 16 should be apertured so as to present no obstacle but the specimen to light above and below the focused area. A multiple filter assembly 20 in the form of a paddlewheel is mounted for rotation about an axis a perpendicular to and spaced from the light path defined between the lamp 12 and the illuminated area on the sample drawer 16. The paddlewheel is typically driven at about 600r.p.m. In the preferred embodiment, three narrow bandwidth plate-shaped optical interference filters 22 are mounted on a hexagonal axle 24. The respective planes of the filters 22 are equally separated angularly by about 120°. The filter extend radially from the axle in planes which intersect approximately in a line conincident with the axis of rotation $a$. The filters 22 extend equal radial distances from the axis $a$. The configuration of the filters 22 on the axle 40 thus resembles the letter Y in cross-section. Opaque vanes can be attached to the ends of the filter to intermittently obstruct the light path.

In FIG. 1, the pulse point output 26 of the paddle-wheel is passed through a counter circuit 30 which can be set as discussed in U.S. Pat. No. 3,861,788 to provide individual control signals corresponding to selected angles in the rotation of the paddlewheel and thus to specific wavelengths of interest. The output of the photodetector 28 is passed to a low noise sensor amplifier 32, which is implemented as shown in U.S. Pat. No. 3,861,788. The output of the sensor amplifier 32 is fed via a logarhythmic amplifier 34 to four sample and hold circuits 36, 38, 40 and 42 gated respectively by four outputs of the settable counter circuit 30. Each sample and hold circuit is gated to store a value of optical density at a selected wavelength. An analog computer 43 receives the output of the sample and hold circuits 36, 38, 40 and 42 to multiply the individual optical densities by constants and to sum the resulting products according to a programmed expression. The value of the resulting expression relative to a predetermined level is related to a property of the specimen.

If linear expressions involving $\Delta OD$ instead of OD were desired, for example, for eight wavelengths, the number of sample and hold circuits could be doubled or the arrangement using a differential amplifier and two stages of sample and hold circuitry could be used as shown in U.S. Pat. No. 3,861,788.

In FIG. 2, the output of the low noise sensor amplifier 32 receiving the photodetector output 28, instead of going to the subsequent analog circuitry in FIG. 1, is fed to analog to digital converter 44. The multibit digital output of the converter 44, representative of transmissivity at the various wavelengths passed by the paddlewheel 20 is fed to the parallel data input of a digital computer 46. The data input of the digital computer 46 is gated by means of the pulse point output 26 which acts as a clock signal. The circuitry in FIG. 2 is inherently superior to that in FIG. 1 for one primary reason: storage capacity.

If the output of the sensor amplifier is digitally encoded into 12 parallel bit channels, and of the 1,000 pulse points per revolution, there are only 100 nonredundant useful points per filter for a total of 300 pulse points which correspond to wavelengths, the amount of digital memory necessary to store values of transmissivity for every one of the 300 wavelengths is only 300 × 12 = 3,600 bits. To store 300 more points for absolute transmissivity without the specimen, the storage capacity should be doubled to 7200 bits. In comparison, the equivalent of the simultaneous storage capacity of the analog equipment in FIG. 1 is only 48 bits. Of course, with the digital embodiment of FIG. 2 in a commercially practical system, one would provide only as much storage as needed and program the input to the digital computer 46 to transfer the output of the converter 44 to memory only for selected pulse points. For example, if only 80 pulse points were needed for computations involving absolute and specimen transmissivity, the amount of storage would be 12 × 2 × 80 = 1920 bits.

The digital computer 46 should be one programmed or programmable to carry out specified arithmetic operations using the stored values of transmissivity as well as a plurality of constant factors which are fed into the computer to carry out a particular formula.

Transmissivity, T, is defined as ratio of the intensity of transmitted light, $I_t$, to the intensity of incident light, $I_i$, at a given wavelength. Absolute transmissivity, $T_{abs}$ is defined as the intensity of light transmitted to the photodetector in the absence of a specimen at a given wavelength.

If the test calls for a reflectance measurement rather than transmittance, one or more photodetectors can be arranged above the sample drawer 16 to receive light reflected from the specimen, as shown in FIG, 1 of U.S. Pat. No. 3,861,788.

Optical density at a given wavelength, e.g., 1935 A and the difference between optical densities at two different wavelengths, e.g., 1935 A and 1680 A are defined as follows:

TI, $OD_{1935} = LOG\ (1/T_{1935})$,
where, TI, $T_{1935} = (I_t/I_i)_{1935}$;
thus, TI, $OD_{1935} - OD_{1680} = \Delta OD = Log\ (T_{1680}/T_{1935}) = Log\ (I_{t1680}/I_{t1935})$.

If one is analyzing water alone with a substance of constant transmissivity, the value of $\Delta OD$ at the wavelengths in the expression above can be used in the following linear expression to arrive at a moisture percentage measurement:

TI, % $H_2O = k_0 + k_1\ \Delta OD$, where $k_0$ and $k_1$ are constants.

As discussed in U.S. Pat. No. 3,861,788 where the specimen contains not just water but other substances of varying transmittance, including for example, protein and oil, the simple expression using one value of $\Delta OD$ is inaccurate. Each of the substances in the specimen has its own spectral absorption curve and thus the overall transmissivity of any given wavelength is affected by the spectral absorption curve of each substance in the specimen. Thus, it has been found that by using characteristic $\Delta OD$'for the spectral absorption curve associated with each substance of primary interest in the expression for just one substance, the results obtained through use of these percentage-determining equations can be correlated more closely with analytical results. For example, as discussed in U.S. Pat., 3,861,788, for agricultural products a more useful expression for moisture percentage is $k_0 = k_1\ (\Delta OD_w) = k_2\ (\Delta OD_o) = k_3\ (\Delta OD_p)$, where, w, 0 and p refer to the characteristic wavelength pairs for water, oil and protein, respectively, at which optical densities are measured and their respective differences obtained.

The following examples illustrate new biomedical applications of spectral transissivity correlation. In each of these tests the basic parameters were chosen, either optical density or the value of dT/T at a particular wavelength, and the values of the parameters for a plurality of sample specimens under observation were recorded for different wavelengths in a computer memory. After the tests were complete, each specimen was analyzed by conventional laboratory techniques to determine whether or not the specimens had a given abnormality such as malignancy. In the case of the fourth example, using cervical cancer, "maybe"was thrown in as a third level variable. Next the affirmative or negative results of the laboratory tests on each individual sample were entered into a computer for correlation analysis with, for instance 300 values of OD stored for each sample. Next came a correlation analysis which is a conventional technique for arriving at an expression involving a mathematical function of the spectral data for any specimen such that the respective values of that expression for all specimens which are affirmative (e.g., malignant) are higher than the respective values of that expression for all specimens which are negative according to the laboratory results. There are many known techniques for correlating two sets of data like the spectral and laboratory data. In all of the examples which follow, except experiment No. 1, the type of correlation used to arrive at the expression known as a correlation equation is multiple linear regression analysis assuming a Gaussian distribution of samples even though the pathology information was only in the form of affirmative and negative conclusions. That is no "degree" or "level" of cancer was stated. It is recognized that a Gaussian assumption is not valid for simple binary data. Nevertheless, this approach appears to work well for selecting the optimum absorption wavelengths as evidenced by the data below.

term is the ratio of the derivative of transmissivity of the specimen at a given wavelength to the absolute transmissivity without the specimen at that wavelength. The parameter $dT/T_{abs}$ is more sensitive than the parameter OD and thus one could expect an improvement in the correlation between the spectral and laboratory data in the first three tests if the parameter $dT/T_{abs}$ was used instead of OD. The parameter $d^2T/T$, that is the second derivative of the specimen transimissivity over the absolute transmissivity, may produce even greater correlation although it is more difficult to instrument. The OD correlation equations generated for the first three experiments could be implemented as shown in FIG. 1. The additional mathematical complexity of the dT/T computation in experiment No. 4 makes analog equipment impractical and necessitates digital instrumentation as shown in FIG. 2.

Figure 3:
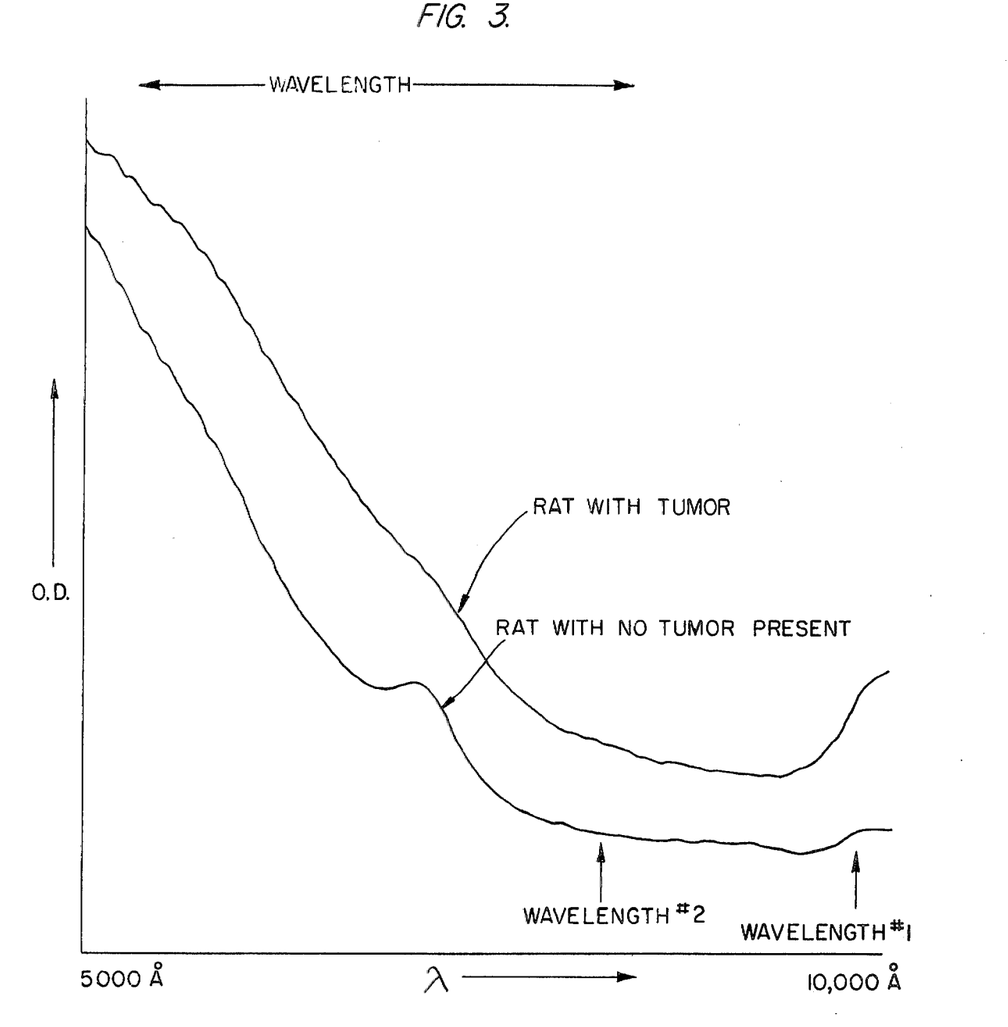
FIG. 3 is a typical graph of optical density versus wavelength for rat livers with and without cancer.
Figure 4:
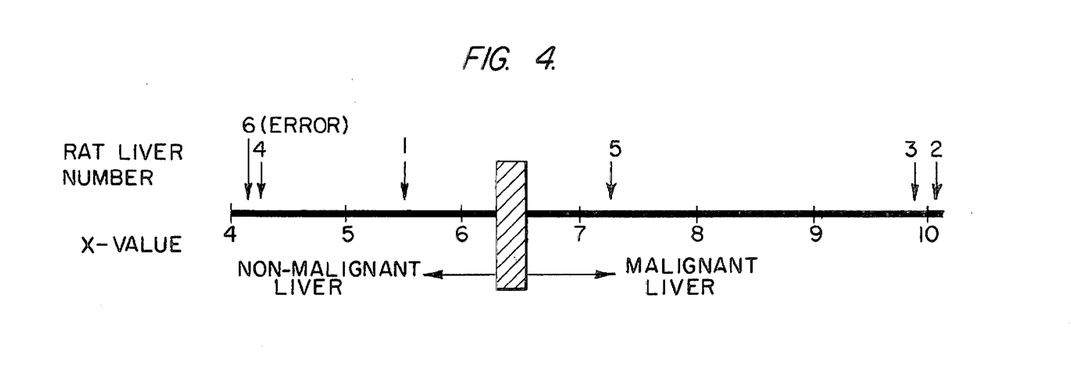
FIG. 4 is a line-plot of x-values of the correlation equation for rat liver cancer.

| Experiment No. 1 | |
| --- | --- |
| Test subjects: | six one-year old male Holzman rats |
| Abnormality: | about half expected to have liver cancer induced by carcinogen pesticide in feed (400 ppm 2 acetyl amino flourene) |
| Optical Instrumentation | |
| Type of illuminator: | Cary-14 monochromator |
| Spectrum: | 5000 – 10,000 A |
| Type of photodetector: | Solid state silicon |
| Maximum OD: | 5.0 |
| Specimens: | surgically removed rat livers |
| Laboratory Analysis: | microscopic pathological examination of each liver after taking spectral data |
| Typical rat liver spectrum: | see FIG. 3 (OD vs. λ) |
| Correlation Wavelengths: | Primary pair: 1 -9575 A 2 -1832 A (see arrows in FIG. 3) |
| Correlation equation: | $X = 17.9 + 69.1\ OD_1 - 53.4\ OD_2$, where 1 and 2 refer to the wavelengths above |
| X-Distribution: | see FIG. 4 |

It is important to recognize that the type of computer on which this correlation analysis is performed is not the type shown in either FIG. 1 or FIG. 2. The apparatus shown in the FIGS. relates to special purpose instrumentation which uses the correlation equation arrived at by means of multiple linear regression analysis performed on another computer with much greater capacity and flexibility.

The following four experiments were run to determine whether useful correlation equations could be produced just for the sample specimens. The subjects of the test were are follows: (1) six rats, some with cancer of the liver; (2) 22 mice, some with cancer of the bladder; (3) 20 vials of 25% normal human serum albumin, some with microorganisms; and (4) 22 cervical scrapings, some with malignancy, some without and some questionable. In the first three experiments, the test parameter was OD. That is, optical instrumentation like that shown at 10 in FIGS. 1 and 2 was used to produce a photodetector output to a sensor amplifier whose output was fed to a logarithmic amplifier before being fed to a digital computer. The fourth test on cervical scrapings used the parameter $dT/T_{abs}$. This A comparison of the correlation equation results with those of simple observation is presented in Table 1 below, where N and C mean normal and cancerous, respectively:

TABLE I

| RAT LIVER NUMBER | 1 | 2 | 3 | 4 | 5 | 6 |
| --- | --- | --- | --- | --- | --- | --- |
| PATHOLOGY RESULTS | N | C | C | N | C | C |
| VISUAL JUDGEMENT | N | C | C | N | C | N |
| CORRELATION EQUATION | N | C | C | N | C | N |

Like FIG. 3, the above table indicates that all samples were correctly predicated except for rat liver No. 6. Because there were only six samples, only a primary pair of wavelengths were found. Thus, the above correlation could not take advantage of multiple linear regression of wavelength pairs. It was noted for these rats that the cancerous livers had higher optical absorptions than the normal ones, probably because the tumor had a different refractive index than the liver and thus increased the scattering of light.

| Experiment No. 2 | |
| --- | --- |
| Test Subjects: | 22 female bulb/c-breed mice |
| Abnormality: | about half expected to have bladder |

-continued

Figure 5:
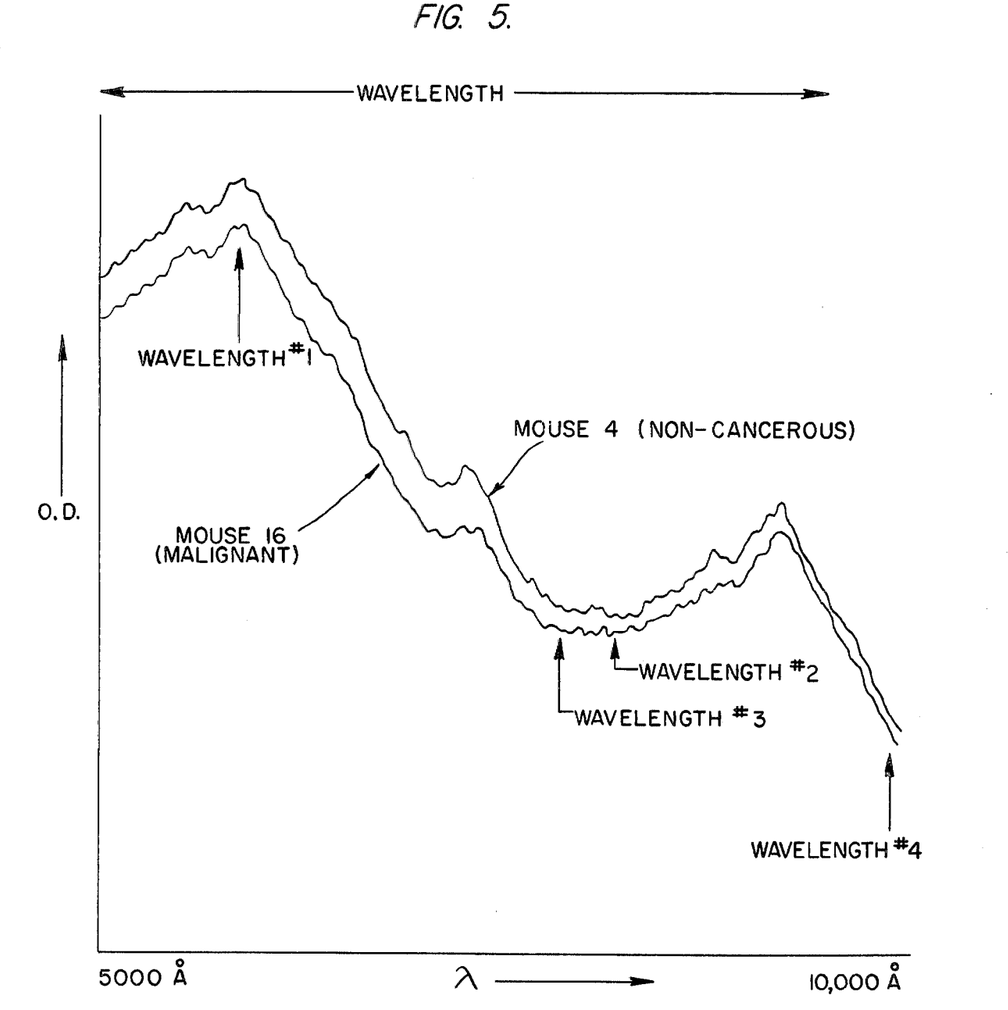
FIG. 5 is a typical graph of optical density versus wavelength for mice with and without cancer.
Figure 6:
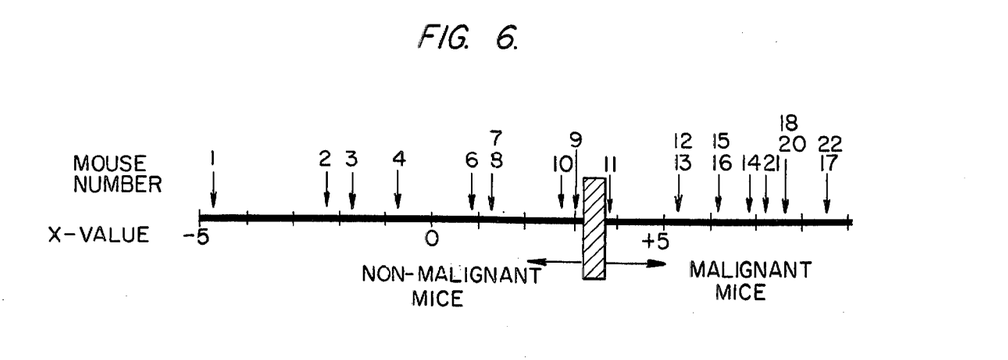
FIG. 6 is a line-plot of x-values of the correlation equation for cancerous mice.

| | Experiment No. 2 |
|---|---|
| | cancer induced by carcinogen pesticide in feed (50–250 ppm 2 acetyl amino flourene) |
| Optical Instrumentation: | same as in Experiment No. 1 |
| Specimens: | whole mice (bladder in vivo) attached in a spreadcalf position to a square metal frame with ventral side facing illuminator |
| Laboratory Analysis: | surgical removal and microscopic pathological examination of each bladder after taking spectral data |
| Typical Mouse Spectrum: | see FIG. 5 (OD vs.λ) |
| Correlation Wavelengths: | Primary Pair: No. 1 5900 A No. 2 8600 A Secondary Pair: No. 3 8200 A No. 4 10620 A |
| Correlation Equation: | $X = 239.1 - [57.2\ OD_1 - 54.2\ OD_2] - [42.3\ OD_3 + 16.0\ OD_4]$ |
| X-Distribution: | see FIG. 6 |

It was possible to do the mice tests in vivo because the transmittance typically produced optical densities below 5.0 OD. Each mouse was anesthetized with ethyl ether and then its feet were tied to the corners of the rectangular frame. The animal was positioned so that the collimated monochromator beam, approximately 5 millimeters in size, intersected the bladder region. The optical energy impacting the mouse was measurable in milliwatts.

The large difference in absorption between 5900 A and about 10,000 A in FIG. 5 was a characteristic separation between malignant and nonmalignant for almost all mice tested. In fact, prior to receiving the pathology results, a "blind test" was performed using all the spectrum traces. This was done by sorting all the spectrum curves into two groups: those with high absorption between 5900 A and 10,000 A, and those with lower absorption. This simple visual judgement proved correct on 20 of the 22 mice; the only "error" was for malignant mice 11 and 12. The results of this visual examination of the spectrum traces is summarized in the "visual" column of TAble II below:

In this experiment, the larger number of test specimens enabled use of two pairs of wavelengths in multiple linear regression analysis to correlate the spectral and pathological data.

The mice and rat data raises the following questions:
1. Is the correlation really relating the spectrum data to the presence of malignancy? Or could it be that the spectrum correlation is actually relating the presence of the pesticide residue that was in the diet of the cancerous mice and rats, or perhaps some side effect due to the pesticide
2. It is usually expected that the presence of an additional layer of material —i.e., malignant cells on the gladder —would cause an increase in "light scattering" because of the cahnge in refractive index. An increase in light scattering should cause the optical density to increase. Yet the spectrum traces for the cancerous mice show a decrease in optical density with the presence of a tumor.

Figure 7:
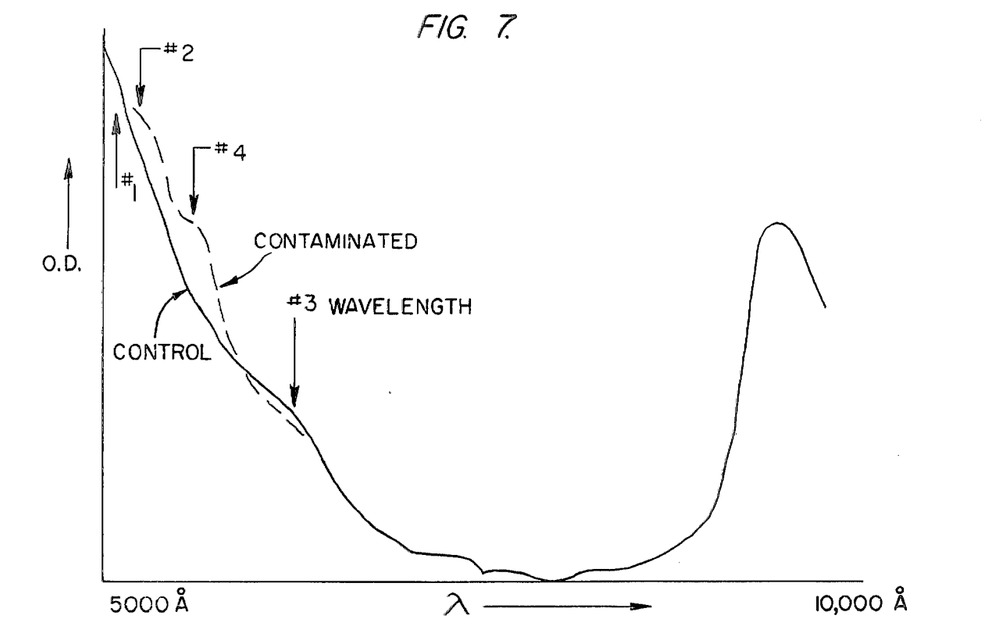
FIG. 7 is a typical graph of optical density versus wavelength for contaminated and control serum.

| | Experiment No. 3 |
|---|---|
| Test Subjects: | 20 50cc glass vials of 25% human serum albumin selected from four different production lots to include any effect of typical color variation (see Table III below) |
| Abnormality: | 80% deliberately contaminated with microorganisms as indicated in Table III; no apparent difference in turbidity (i.e., cloudiness) between control and contaminated samples |
| Optical Instrumentation: | same as in Experiment No. 1 |
| Specimens: | each sample was analyzed without removal from the vial; light beam intersected cylindrical axis of vial at right angles |
| Laboratory analysis: | concentration of microorganism known beforehand |
| Typical albumin spectrum: | see FIG. 7 (OD vs. λ) |
| Correlation Wavelengths: | Primary Pair: No. 1   −5034 A No. 2   −5374 A Secondary Pair: No. 3   −6258 A No. 4   −5731 A |
| Correlation Equation: | $X = 9.41 + [64.4\ OD_{1\ -251.1\ OD2}] - [86.2\ OD_{3\ -273.6\ OD4}]$ |

TABLE II

| MOUSE NUMBERS | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| PATHOLOGY RESULTS | N | N | N | N | N | N | N | N | N | N | C | C | C | C | C | C | C | C | C | C | C | C |
| VISUAL JUDGMENT | N | N | N | N | N | N | N | N | N | N | N | N | C | C | C | C | C | C | C | C | C | C |
| CORRELATION EQUATION | N | N | N | N | N | N | N | N | N | N | C | C | C | C | C | C | C | C | C | C | C | C |

Experiment No. 3 demonstrates that light transmission can be used as a high speed sorting means of separating contaminated vials on the production line.

Control and contaminated samples are arbitrarily given the nominal values one and ten respectively. In Table III below, the "computed" column represents the value, X, of the correlation expression for the given sample. The "difference" column indicates how close the computed value came to the nominal value. There is a clear separation (screening limit) between the control versus the contaminated samples; the highest computed X-value for a control sample is 5.996 and the lowest for the contaminated samples is 6.310. This separation appears to be statistically significant.

TABLE III

| VIAL NUMBER | IDENTIFICATION CODE* | TYPE BACTERIA | BACTERIA CONCENTRATION |
|---|---|---|---|
| 1 | 1 - 0 | Control | None |
| 2 | 2 - 0 | Control | None |
| 3 | 3 - 0 | Control | None |
| 4 | 4 - 0 | Control | None |
| 5 | 1 - 1 | P. aeroguosa | $6.0 \times 10^6$ ORG/ML |
| 6 | 2 - 1 | P. aeroguosa | $6.0 \times 10^6$ ORG/ML |
| 7 | 3 - 1 | P. aeroguosa | $6.25 \times 10^6$ ORG/ML |
| 8 | 4 - 1 | P. aeroguosa | $4.7 \times 10^6$ ORG/ML |
| 9 | 1 - 3 | S. aureus | $3.6 \times 10^7$ ORG/ML |
| 10 | 2 - 3 | S. aureus | $1.25 \times 10^7$ ORG/ML |
| 11 | 3 - 3 | S. aureus | $5.35 \times 10^6$ ORG/ML |
| 12 | 4 - 3 | S. aureus | $9.0 \times 10^6$ ORG/ML |
| 13 | 1 - 5 | Bacillus sp. | $1.0 \times 10^6$ ORG/ML |
| 14 | 2 - 5 | Bacillus sp. | $9.8 \times 10^5$ ORG/ML |
| 15 | 3 - 5 | Bacillus sp. | $8.7 \times 10^5$ ORG/ML |
| 16 | 4 - 5 | Bacillus sp. | $1.17 \times 10^6$ ORG/ML |
| 17 | 1 - 7 | Unidentified (−) | $5.7 \times 10^6$ ORG/ML |
| 18 | 2 - 7 | Unidentified (−) | $4.6 \times 10^5$ ORG/ML |
| 19 | 3 - 7 | Unidentified (−) | $2.8 \times 10^5$ ORG/ML |
| 20 | 4 - 7 | Grain - bacilli | $1.8 \times 10^6$ ORG/ML |

| VIAL NUMBER | X-VALUE COMPUTED | | NOMINAL | DIFFERENCE |
|---|---|---|---|---|
| 1 | 2.163 | Control | 1.000 | 1.163 |
| 2 | 5.299 | | 1.000 | 4.299 |
| 3 | 5.996 | | 1.000 | 4.996 |
| 4 | 0.9273 | | 1.000 | −.07265 |
| 5 | 9.916 | | 10.00 | −.08366 |
| 6 | 9.025 | | 10.00 | −.9750 |
| 7 | 9.854 | | 10.00 | −.1456 |
| 8 | 9.747 | | 10.00 | −.2531 |
| 9 | 6.310 | | 10.00 | −3.690 |
| 10 | 6.607 | | 10.00 | −3.393 |
| 11 | 7.187 | | 10.00 | −2.813 |
| 12 | 7.677 | | 10.00 | −2.323 |
| 13 | 18.25 | | 10.00 | −0.2526 |
| 14 | 9.156 | | 10.00 | −0.8442 |
| 15 | 8.908 | | 10.00 | −1.092 |
| 16 | 9.503 | | 10.00 | −0.4975 |
| 17 | 11.62 | | 10.00 | 1.618 |
| 18 | 10.91 | Contaminated | 10.00 | 0.9678 |
| 19 | 10.63 | | 10.00 | 0.6321 |
| 20 | 12.32 | | 10.00 | 2.316 |

* first digit is lot number

Figure 8:
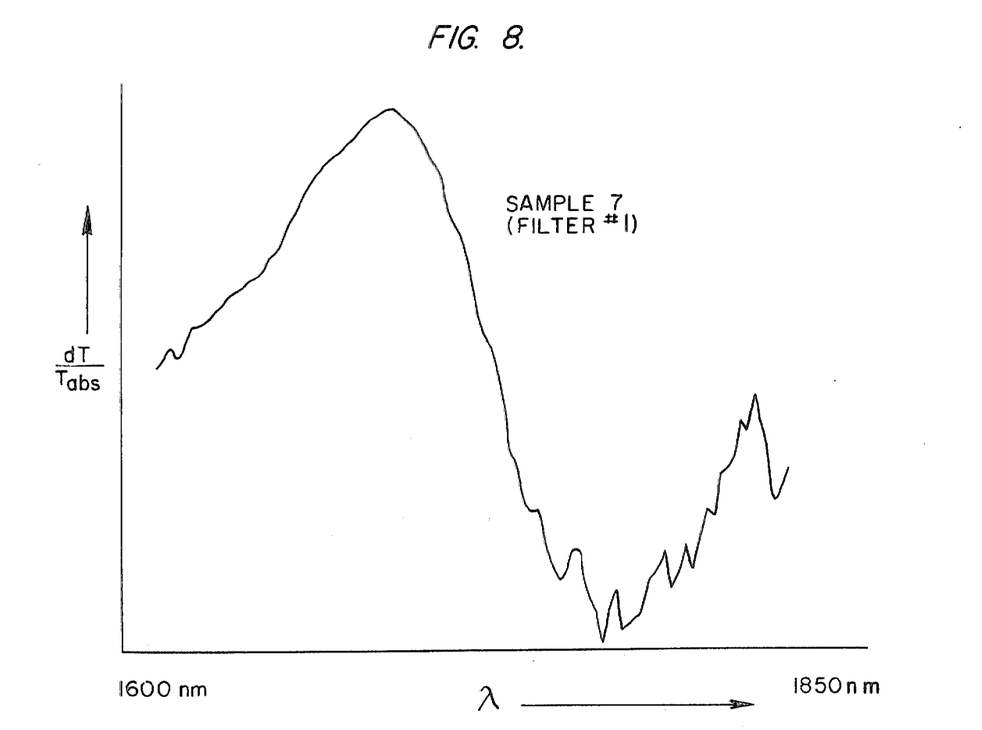
FIG. 8 is a typical graph of dT/T versus wavelength for a nonmalignant cervical scraping.

| Experiment No. 4 | |
|---|---|
| Test Subjects: | 22 human cervical scrapings |
| Abnormality: | 4 samples malignant; 6 others had atypical cells |
| Optical Instrumentation: | same as at 10 in FIGS. 1 and 2 |
| Type of Illuminator: | paddlewheel 20 |
| Spectrum: | 1600 nm to 2350 nm |
| Type of Photodetector: | solid state silicon |
| Maximum OD: | 5.0 |
| Specimen: | scrapings suspended in 2.5 ml, 50% ethyl alcohol, 50% distilled water in optically flat bottom cup (equivalent thickness of the solution was 1.5 mm). |
| Laboratory Analysis: | conventional diagnostic cytology prior to taking spectral data |
| Typical Cervical Scraping Spectrum: | see FIG. 8 ($dT/T_{abs}$ vs. λ) |
| Correlation Wavelengths Using 22 Samples to Compute 5 Constants: | Primary Pair: No. 1 No. 2 Secondary Pair: No. 3 No. 4 |
| Corresponding Correlation Equation: | $X_1 = 9.998 - 16140 (dT/T) - 10190 (dT/T)_2 + 5624 (dT/T)_3 - 6580 (dT/T)_4$ |
| Correlation Wavelengths | |

-continued

| Experiment No. 4 | |
|---|---|
| Using 16 Samples (Without Nos. 14, 15, 16, 18, 20, 21): | Primary Pair No. 1 No. 2 Secondary Pair No. 3 No. 4 |
| Corresponding Correlation Equation: | $X_2 = 9.349 - 25780(dT/T)_1 - 9242(dT/T)_2 + 26800(dT/T)_3 - 7920(dT/T)_4$ |

Experiment No. 4 demonstrates the potential of light transmittance analysis as a rapid screening method for cervical cytology samples used in the detection of uterine cancer. The previously studied samples were assigned nominal values of 1,6 and 10 to indicate, respectively, that they were malignant, questionable or non-malignant. These laboratory values were then correlated with the spectral data for $dT/T_{abs}$ by multiple linear regression analysis assuming Gaussian distribution even though the sample population was not necessarily normal. On the computer, the dT/T values are produced by plotting all 300 values of transmittance, T, developing an equation to fit the plotted curve, taking the first derivative of the equation, and computing the value of all $dT/T_{abs}$ over all 300 discrete wavelengths. As discussed below, this procedure differs from a practical instrumentation approach to deriving the values of $dT/T_{abs}$, for instance, at four different wavelengths.

The term dT/T was chosen over OD because it produces more sensitive low noise data analysis. A second derivative term $d^2T/T_{abs}$ could also be used for this purpose.

Table IV below summarizes the results of the correlations using the $X_1$ and $X_2$ correlation equations.

as positive samples. The one questionable sample that would have been sorted as negative, Sample 18, is from a patient that had squamous carcinoma that was treated with radiation and sub-total hysterectomy. This sample had some atypyical cells that might be due to healing.

It is noted that expanding the spectrum down to at least 1000 nm will allow thicker samples and even less

TABLE IV

| | | | Equation No. 1 | | | Equation No. 2 | |
| | | | Malignancy | | | | |
| Sample Number | Classification | Patient History | Nominal | X-Value Computed | Difference | X-Value Computed | Difference |
|---|---|---|---|---|---|---|---|
| 1 | Cervicitis | None | 10.00 | 10.54 | 0.5427 | 9.243 | −0.7569 |
| 2 | Cervicitis | None | 10.00 | 8.928 | −1.072 | 9.921 | −.07321 |
| 3 | Cervicitis-Trichomonas | None | 10.00 | 10.28 | 0.2780 | 6.965 | −1.835 |
| 4 | Cervicitis | None | 10.00 | 8.925 | −1.075 | 9.352 | −0.6421 |
| 5 | Normal | None | 10.00 | 10.77 | 0.7717 | 12.37 | 2.374 |
| 6 | Cervicitis-Trichomonas | None | 10.00 | 9.842 | −0.1585 | 6.937 | −3.063 |
| 7 | Cervicitis-Trichomonas | None | 10.00 | 9.164 | −0.8356 | 10.42 | 0.4213 |
| 8 | Cervicitis-Trichomonas | None | 10.00 | 7.421 | −2.576 | 11.76 | 1.761 |
| 9 | Cervicitis | None | 10.00 | 9.123 | −0.8769 | 6.583 | −3.417 |
| 10 | Cervicitis-Trichomonas | None | 10.00 | 8.618 | −1.382 | 8.339 | −1.661 |
| 11 | Squamous cell carcinoma | Untreated invasive squamous cell carcinoma | 1.000 | 4.734 | 3.734 | 3.317 | 2.317 |
| 12 | Uterina sarcoma | | 1.000 | 3.628 | 3.620 | 2.008 | 1.808 |
| 13 | Normal | Adenocarcinoma, endometrium | 10.00 | 3.820 | −6.180 | 5.453 | 4.547 |
| 14 | Atypical eithelial cells | Radiation therapy for Squamous cell carcinoma | 6.000 | 7.443 | 1.443 | | |
| 15 | Atypical epithelial cells | Radiation therapy for squamous cell carcinoma | 6.000 | 7.439 | 1.439 | | |
| 16 | Atypical epithelial cells | Radiation therapy for squamous cell carcinoma | 6.000 | 3.442 | −2.588 | | |
| 17 | Inflammation | ? malignancy | 10.00 | 8.154 | −1.846 | 9.977 | .02259 |
| | Atypical epithelial cells | Radiation therapy for squamous cell carcinoma | 6.000 | 8.453 | 2.453 | | |
| 19 | Squamous cell carcinoma, cervix | Untreated squamous cell carcinoma | 1.000 | 4.740 | 3.740 | 6.568 | 5.568 |
| 20 | - Very bloody - endometrial cells present | ? malignancy | 6.000 | 5.425 | −0.5738 | | |
| 21 | Atypical epithelial cells | Vulvectomy for squamous cell carcinoma, vulva | 6.000 | 7.748 | 1.748 | | |
| 22 | Squamous cell carcinoma | Untreated squamous cell | 1.000 | 1.364 | 0.3645 | 2.774 | 1.774 |

Using the $X_1$ correlation data with a screening limit of approximately 8.6, there would be 25% false positives (3 out of 12), all six questionable samples as well as all 4 positive samples would have to be screened as suspected positives.

It may be interesting to note, that Sample 13 which has the strongest false positive is from a patient that had cancer of the endometrium which rarely show up in cervical scraping. Also, Sample 16 of the "questionable" group showed up strongly positive, although no cancerous cells were uncovered in diagnostic cytology. This patient had had radiation treatment for cancer of the cervix. Furthermore, Sample 22, to which the $X_1$ correlation equation gave the strongest positive indication is from a patient with untreated cancer.

The $X_2$ correlation equation was based only on the 16 samples that the clinical analysis indicated were definitive (10 negative samples and 4 positive samples). Thus, the optimum wavelengths and correlation coefficients were derived assuming an arbitrary value of 10.0 for the negatives and 1.0 for the positives.

Using the $X_2$ equation with the screening limit remaining at 8.6, there would be 33% (4 out of 12) false positives; five out of six questionable samples and all four of the positive samples would have been screened instrument noise. Larger sample populations should of course be included and more sophisticated data reduction techniques (non-linear regression; $d^2T$, etc.) should be evaluated.

PRACTICAL INSTRUMENTATION

The illustrative correlation equations developed in the foregoing examples are used by the devices shown in FIGS. 1 and 2. In the experiments 1, 2 and 3 using OD expressions, the value of the given correlation expressions are computed on analog equipment since data from only a small number of wavelengths are required. Thus, for example, in testing mice, the analog computer 43 would be programmed to compute the value of the linear expression $239.1 - 57.2 \, OD_1 = 54.2 OD_2 - 42.3 OD_3 = 16.0 d_4$, the OD values being supplied for a given mouse by the sample and hold circuits 36, 38, 40 and 42. The wavelengths 1, 2, 3 and 4 are selected by setting the counter circuit 30 to provide gating signals to the respective ssmple and hold circuits at the corresponding pulse points produced by the paddlewheel filter assembly 20.

In implementing the dT/T correlation equation of experiment No. 4, the digital system of FIG. 2 provides the needed storage capacity. The simple arithmetic of the linear expression could be carried out easily by an analog computer. However, unlike OD, which is derived in one logarythmic conversion, $dT/T_{abs}$ requires computation of the slope of the transmissivity curve at each wavelength and thus much more data is required. A preferred approach with limited digital storage is to average the difference between 10 pairs of points on either side of wavelength 1, as illustrated in the following program outline:

1. Enter the values of $\lambda_w$, $\lambda_x$, $\lambda_y$, $\lambda_z$ and $k_0$, $k_1$, $k_2$, $k_3$, $k_4$.

2. With no specimen, store 80 $T_{abs}$ values as follows:
   $\lambda_{w-10}'$, $\lambda_w'$, $\lambda_{w+9}$; $\lambda_{x-10}'$, $\lambda_x'$, $\lambda_{x+9}$, $\lambda_{y-10}'$, $\lambda_y'$, $\lambda_{y+9}$, $\lambda_{z-10}'$, $\lambda_z'$, $\lambda_{z+9}$ 3. With specimen in place, repeat step 2 for 80 T values.

4. Compute $\sum_{m=1}^{10} T\lambda_{w-m} - \sum_{m=0}^{9} T\lambda_{w+m} \approx 20\, dT\lambda_w$ 5. Store $20\, dT\lambda_w$.

6. Compute $\sum_{m=-10}^{9} T_{abs}\lambda_{w+m} \approx 20\, T_{abs}\lambda$

7. Store $20\, T_{abs}\lambda_w$.

8. Compute $20\, dT\lambda_w \div 20\, T_{abs}\lambda_w = (dT/T_{abs})\lambda_w$.

9. Store $(dT/T_{abs})\lambda_w$.

10. Repeat steps 4–9 for $\lambda_x$, $\lambda_y$ and $\lambda_z$.

11. Compute $k_0 + k_1(dT/T_{abs})\lambda_w + k_2(dT/Tabs)\lambda_{x''} + k_4(dT/T_{abs})\lambda_z$.

Another application of the above described principle is the use of light transmittance directly through fertilized eggs to determine whether the embryo is alive.

The above described embodiments and examples relating to the invention are intended to be illustrative, not restrictive. For example, reflectance can be used instead of transmittance. The scope and spirit of the invention are indicated by the appended claims and all equivalents thereto are intended to be embraced therein.

I claim:

1. A method of detecting pathological abnormality in a multicellular bulk biomedical specimen comprising the steps of recording and analyzing light absorption spectrum data of the multicellular bulk specimen in accordance with a mathematical expression which correlates the spectrum data of a multiplicity of corresponding biomedical samples with the results of typing of said samples by clinical pathology.

2. A method of detecting the presence of a pathological abnormality in a multicellular bulk biomedical specimen, comprising the steps of illuminating the multicellular bulk specimen sequentially with a plurality of difference light wavelengths, recording selected light absorption dependent values within the sample's light output spectrum, computing the value of a mathematical function of said selected absorption-dependent values, said mathematical function being selected to produce a computed value which correlates with the presence or absence of said pathological abnormality, and comparing the level of the computed value to a predetermined screening level.

3. The method of claim 2, wherein said absorption-dependent values are light transmittance-dependent values.

4. The method of claim 3, wherein said transmittance-dependent values are optical density values at selected wavelengths.

5. The method of claim 3, wherein each said transmittance-dependent value is the ratio of a derivative of the transmittivity of the specimen and absolute transmissivity at a selected wavelength.

6. The method of claim 2, wherein said pathological abnormality is malignancy and said specimen is animal tissue.

7. The method of claim 6, werein each said absorption-dependent value is the ratio of a derivative of the transmissivity of the specimen and absolute transmissivity at a selected wavelength.

8. The method of claim 6, wherein said animal tissue is human cervical tissue.

9. The method of claim 6, wherein said animal tissue is rat liver tissue.

10. The method of claim 6, wherein said animal tissue is mouse bladder tissue.

11. The method of claim 6, wherein said animal tissue is human female reproductive organ tissue.

12. The method of claim 2, wherein said specimen is serum and said pathological abnormality therein is bacterial contamination.

13. The method of claim 2, wherein said wavelengths are all greater than 5,000 A.

* * * * *

UNITED STATES PATENT OFFICE
CERTIFICATE OF CORRECTION

Patent No. 4,017,192     Dated April 12, 1977

Inventor(s)  Robert D. Rosenthal

It is certified that error appears in the above-identified patent and that said Letters Patent are hereby corrected as shown below:

Column 1, line 8, "Eugene R. Gannssle" should read --Eugene R. Ganssle--.

Column 2, line 65, "filter" should be --filters--;

line 67, "conincident" should be --coincident--.

Column 4, line 16, "TI" should be deleted;

line 17, "TI" should be deleted;

line 18, "TI" should be deleted;

line 25, "TI" should be deleted;

line 36, "$\Delta OD$'for" should read --$\Delta OD$'s for--;

lines 43-44, "$k_0 = K_1 (\Delta OD_w) = k_2 (\Delta OD_0) = k_3$" should read --$k_0 + k_1 (\Delta OD_w) + k_2 (\Delta OD_0) + k_3$--.

Column 5, line 51, "are" should be changed to --as--.

Column 6, lines 9 and 10, "transimissivity" should read --transmissivity--;

line 55, "predicated" should read --predicted--.

UNITED STATES PATENT OFFICE
CERTIFICATE OF CORRECTION

Patent No. 4,017,192      Dated April 12, 1977

Inventor(s)     Robert D. Rosenthal

It is certified that error appears in the above-identified patent and that said Letters Patent are hereby corrected as shown below:

Column 7, line 42 "TAble II" should read --Table II--;

line 67, "gladder" should be --bladder--;

line 68, "cahnge" should be --change--.

Column 11, line 51, "show" should be --shows--;

line 56, "X," should be --$X_1$--.

Column 12, lines 58-59, "239.1 - 57.2 $OD_1$ = 54.2 $OD_2$ - 42.3 $OD_3$ = 16.0 $OD_4$" should read --239.1 - 57.2 $OD_1$ + 54.2 $OD_2$ - 42.3 $OD_3$ + 16.0 $OD_4$--;

line 63 "ssmple" should be --sample--.

Column 13, line 58, "difference" should be --different--.

UNITED STATES PATENT OFFICE
CERTIFICATE OF CORRECTION

Patent No. 4,017,192          Dated April 12, 1977

Inventor(s) Robert D. Rosenthal

It is certified that error appears in the above-identified patent and that said Letters Patent are hereby corrected as shown below:

Column 14, line 39, "transmittivity" should read -- transmissivity --.

line 44, "wcrein" should read -- wherein --.

Signed and Sealed this twenty-sixth Day of July 1977

[SEAL]

Attest:

RUTH C. MASON
*Attesting Officer*

C. MARSHALL DANN
*Commissioner of Patents and Trademarks*